(12) United States Patent
Kokate et al.

(10) Patent No.: US 6,514,214 B2
(45) Date of Patent: Feb. 4, 2003

(54) INTRAVASCULAR TEMPERATURE SENSOR

(75) Inventors: Jaydeep Y. Kokate, Maple Grove, MN (US); Eric M. DoBrava, Crystal, MN (US); Marwane S. Berrada, Minneapolis, MN (US); Scott Kimmel, Saint Paul, MN (US); Suzana Prstic, Minneapolis, MN (US); Michael F. Hoey, Shoreview, MN (US); Avram Bar-Cohen, Saint Louis Park, MN (US); Paul A. Iaizzo, White Bear Lake, MN (US)

(73) Assignee: SciMed Life Systems, Inc., Maple Grove, MN (US)

( * ) Notice: Subject to any disclaimer, the term of this patent is extended or adjusted under 35 U.S.C. 154(b) by 11 days.

(21) Appl. No.: 09/782,502
(22) Filed: Feb. 13, 2001
(65) Prior Publication Data
US 2002/0111560 A1 Aug. 15, 2002

(51) Int. Cl.⁷ .................................. A61B 5/00
(52) U.S. Cl. ........................ 600/549; 600/505
(58) Field of Search ................. 600/407, 585, 600/433–435, 473, 474, 479, 549, 504, 505; 604/96.01, 915; 374/100, 112

(56) References Cited

U.S. PATENT DOCUMENTS

| | | | |
|---|---|---|---|
| 3,273,395 A | 9/1966 | Schwarz | 374/133 |
| 3,866,599 A | 2/1975 | Johnson | 600/342 |
| 3,913,568 A | 10/1975 | Carpenter | 600/142 |

(List continued on next page.)

FOREIGN PATENT DOCUMENTS

| | | |
|---|---|---|
| EP | 0 856 278 A2 | 8/1998 |
| WO | WO 97/10748 | 3/1997 |
| WO | WO 00/27278 | 5/2000 |
| WO | WO 00/54673 | 9/2000 |

OTHER PUBLICATIONS

Buja et al., "Role of Inflammation in Coronary Plaque Disruption," *Circulation*, vol. 89, No. 1, Jan. 1994, pp. 503–505.
Casscells et al., "Thermal Detection of Cellular Infiltrates in Living Atherosclerotic Plaques: Possible Implications for Plaque Rupture and Thrombosis," *The Lancet*, vol. 347, May 25, 1995, pp. 1447–1449.
Davies, M.J., "Detecting Vulnerable Coronary Plaques," *The Lancet*, vol. 347, May 25, 1996, pp. 1422–1423.
Falk et al., "Coronary Plaque Disruption," *Circulation*, vol. 92, No. 3, Aug. 1, 1995, pp. 657–671.
Muller et al., "Triggers, Acute Risk Factors and Vulnerable Plaques: The Lexicon of a New Frontier," *JACC*, vol. 23, No. 3, Mar. 1, 1994, pp 809–813.
van der Wal et al., Site of Intimal Rupture or Erosion of Thrombosed Coronary Atherosclerotic Plaques is Characterized by an Inflammatory Process Irrespective of the Dominate Plaque Morphology, *Circulation*, vol. 89, No. 1, Jan. 1994, pp. 36–44.

*Primary Examiner*—Kevin Shaver
*Assistant Examiner*—Charles Marmor, II
(74) *Attorney, Agent, or Firm*—Fish & Richardson P.C., P.A.

(57) ABSTRACT

Devices and methods for detecting vulnerable plaque within a blood vessel are disclosed. A catheter in accordance with the present invention includes an elongate shaft having a proximal end, a distal end, and an outer surface. At least one temperature sensor is disposed proximate to the distal end of the elongate shaft. In one preferred embodiment, the at least one temperature sensor is adapted to contact an inner surface of the blood vessel. In another preferred embodiment, at least one temperature sensor is disposed within a channel defined by a body member that is disposed about the elongate shaft.

33 Claims, 6 Drawing Sheets

U.S. PATENT DOCUMENTS

| | | | |
|---|---|---|---|
| 4,005,605 A | 2/1977 | Michael | 374/129 |
| RE32,204 E | 7/1986 | Halvorsen | 600/374 |
| 4,602,642 A | 7/1986 | O'Hara et al. | 600/474 |
| 4,699,147 A | 10/1987 | Chilson et al. | 600/374 |
| 4,752,141 A | 6/1988 | Sun et al. | 374/161 |
| 4,776,334 A | 10/1988 | Prionas | 606/42 |
| 4,777,955 A | 10/1988 | Brayton et al. | 600/374 |
| 4,784,149 A | 11/1988 | Berman et al. | 600/474 |
| 4,790,324 A | 12/1988 | O'Hara et al. | 600/474 |
| 4,794,931 A | 1/1989 | Yock | 600/439 |
| 4,797,840 A | 1/1989 | Fraden | 702/104 |
| 4,841,981 A | 6/1989 | Tanabe et al. | 600/505 |
| 4,862,887 A | 9/1989 | Weber et al. | 606/15 |
| 4,986,671 A | 1/1991 | Sun et al. | 374/131 |
| 4,995,398 A | 2/1991 | Turnidge | 600/508 |
| 5,000,185 A | 3/1991 | Yock | 600/459 |
| 5,046,501 A | 9/1991 | Crilly | 600/477 |
| 5,057,105 A | 10/1991 | Malone et al. | 606/28 |
| 5,057,106 A | 10/1991 | Kasevich et al. | 606/33 |
| 5,109,859 A | 5/1992 | Jenkins | 600/439 |
| 5,174,299 A | 12/1992 | Nelson | 600/505 |
| 5,217,456 A | 6/1993 | Narciso, Jr. | 606/15 |
| 5,237,996 A | 8/1993 | Waldman et al. | 600/374 |
| 5,275,594 A | 1/1994 | Baker et al. | 606/12 |
| 5,279,565 A | 1/1994 | Klein et al. | 604/105 |
| 5,304,173 A | 4/1994 | Kittrell et al. | 606/15 |
| 5,313,949 A | 5/1994 | Yock | 600/467 |
| 5,336,178 A | 8/1994 | Kaplan et al. | 604/509 |
| 5,373,849 A | 12/1994 | Maroney et al. | 600/463 |
| 5,445,157 A | 8/1995 | Adachi et al. | 600/474 |
| 5,542,915 A | 8/1996 | Edwards et al. | 604/22 |
| 5,547,472 A | 8/1996 | Onishi et al. | 604/163.01 |
| 5,558,093 A | 9/1996 | Pomeranz | 600/437 |
| 5,606,974 A | 3/1997 | Castellano et al. | 600/462 |
| 5,623,940 A | 4/1997 | Daikuzono | 600/439 |
| 5,682,899 A | 11/1997 | Nashef et al. | 600/505 |
| 5,733,739 A | 3/1998 | Zakim et al. | 435/29 |
| 5,792,070 A * | 8/1998 | Kauphusman et al. | 600/549 |
| 5,849,028 A | 12/1998 | Chen | 607/102 |
| 5,871,449 A | 2/1999 | Brown | 600/474 |
| 5,906,363 A | 5/1999 | Reis et al. | 269/21 |
| 5,924,997 A | 7/1999 | Campbell | 600/549 |
| 5,935,075 A | 8/1999 | Casscells et al. | 600/474 |
| 5,957,961 A | 9/1999 | Maguire et al. | 607/99 |
| 6,162,184 A | 12/2000 | Swanson et al. | 600/549 |
| 6,197,021 B1 | 3/2001 | Panescu et al. | 606/31 |
| 6,245,026 B1 * | 6/2001 | Campbell et al. | 600/549 |
| 2001/0053882 A1 * | 12/2001 | Haddock et al. | 600/549 |

* cited by examiner

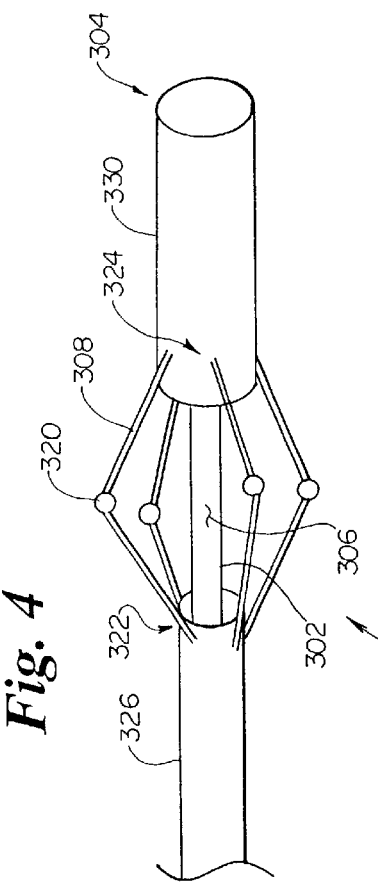
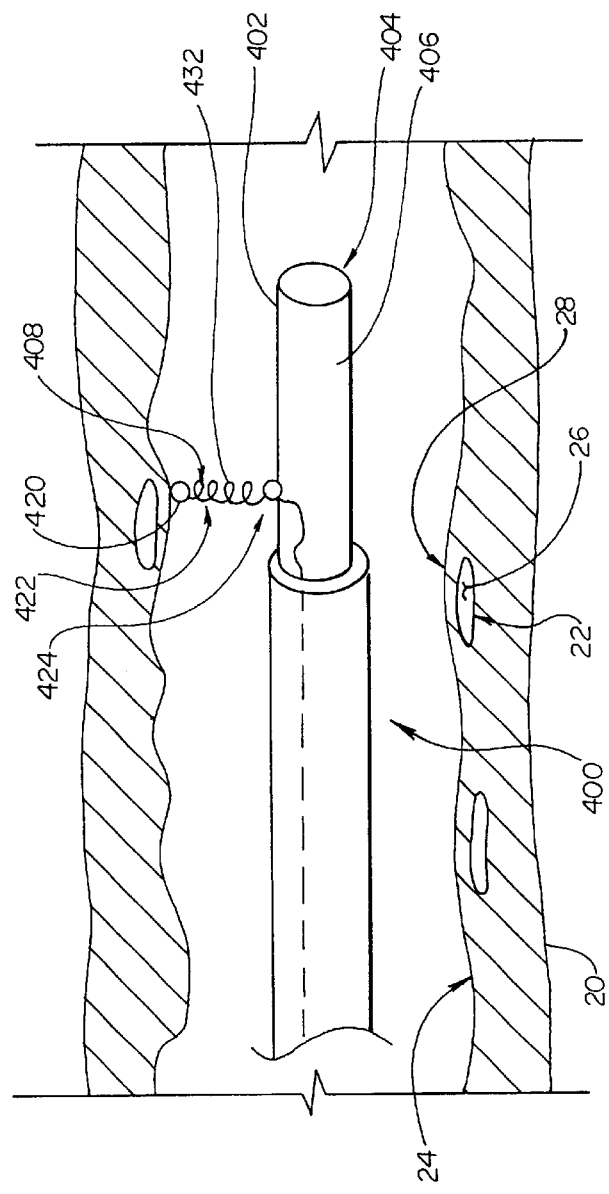
Fig. 4
Fig. 5

INTRAVASCULAR TEMPERATURE SENSOR

FIELD OF THE INVENTION

The present invention relates generally to medical devices for detecting cardiac disease. More particularly, the present invention relates to medical devices for detecting vulnerable plaque within a blood vessel.

BACKGROUND OF THE INVENTION

Therapy modalities for heart disease have traditionally focused on treating blood vessels which have become occluded (blocked) or stenotic (narrowed) by calcified plaque deposits. Blood vessels which have become occluded or stenotic in this manner may interrupt the blood flow which supplies oxygen to the heart muscle. Occluded or stenotic blood vessels may be treated with a number of medical procedures including angioplasty and atherectomy. Angioplasty techniques such as percutaneous transluminal angioplasty (PTA) and percutaneous transluminal coronary angioplasty (PTCA) are relatively noninvasive methods of treating restrictions in blood vessels. In these procedures, a balloon catheter is advanced over a guidewire until the balloon is positioned proximate to a restriction in a diseased vessel. The balloon is then inflated and the restriction in the vessel is stretched. During an atherectomy procedure, the stenotic lesion is mechanically cut or abraded away from the blood vessel wall using an atherectomy catheter.

Calcified plaque deposits typically comprise hard materials. But, plaque may also comprise soft materials or combinations of soft and hard materials. Soft plague typically comprises deposits of cholesterol and other fats which build up within the blood vessels as a patient ages. The build up of plaque in the blood vessels is sometimes referred to as atherosclerosis, or hardening of the arteries.

Atherosclerosis often begins as a small injury to an artery wall. This injury triggers a cascade of injury and response, inflammation, and healing, which may ultimately lead to the narrowing of the artery. As the atherosclerotic plaque worsens, inflammatory cells, especially macrophages, collect, at the site to isolate, the debris of the damaged tissue. The result is a core of lipid, macrophages or foam cells and nectrotic tissue, covered by a thin fibrous cap of scar tissue. If the fibrous cap becomes weakened or is subjected to excessive mechanical stress, it may rupture, exposing the thrombogenic damaged endothelium and metabolic byproducts to the blood stream. If the resulting blood clot is severe enough, it may occlude the artery. If this obstruction persists in a coronary artery, a myocardial infarction or angina may result.

Plaque deposits which are at risk of rupturing are sometimes referred to as vulnerable plaque. Vulnerable plaque typically comprises a core of soft materials covered with a fibrous cap. Many vulnerable plaque deposits do not limit the flow of blood through the blood vessels. It has recently been appreciated that vulnerable plaques which do not limit flow may be particularly dangerous because they can rupture suddenly causing heart attack and death. This may occur, for example, when the vulnerable plaque ruptures and a blood clot is formed inside the blood vessel lumen causing a blockage.

Recently, the pivotal role of inflammation in the progression of atherosclerosis has been recognized. A systemic increase in temperature is often associated with infection (e.g., a fever). Likewise, a local infection or localized damage to tissue may result in a localized increase in temperature. An increase in temperature is thought to be caused by the response of the immune system to infection, known as inflammation and an increase in metabolic activity involved in the healing process. It has been observed that the inflamed necrotic core of a vulnerable plaque maintains itself at a temperature which may be one or more degrees Celsius higher than the surrounding tissue. For example, an inflamed plaque in a human heart, where the normal temperature is about 37° C. may be at a temperature as high as 40° C.

SUMMARY OF THE INVENTION

The present invention relates generally to medical devices for detecting cardiac disease. More particularly, the present invention relates to medical devices for detecting vulnerable plaque within a blood vessel. A catheter in accordance with one embodiment of the present invention includes an elongate shaft and a plurality of arms fixed to the elongate shaft.

The arms preferably have an extended position and a retracted position. A sensor is fixed to each arm proximate a first end thereof. In a preferred embodiment, each sensor contacts the inner surface of a blood vessel when the arms are in the extended position. In a preferred embodiment, a sheath is disposed about the elongate shaft. The arms may be urged into the retracted position by advancing the sheath distally along the elongate shaft.

The signal from each sensor may be displayed and/or recorded using a suitable instrument. Variations in these signals may be noted as the catheter is moved proximally and/or distally-through the blood vessel thermally mapping the transversed region. The variations in the sensor signal may be correlated with the axial position of the catheter. This information may be used to identify the position of any vulnerable plaque deposits in the blood vessel.

In a preferred embodiment, the arms of the catheter expand radially away from the elongate shaft. The angular orientation of plaque deposits within the blood vessel may be identified by observing variations between the signals from the different sensors. For example, sensors which are proximate to vulnerable plaque deposits may read higher temperatures than sensors which are not proximate to vulnerable plaque deposits.

A catheter in accordance with an additional embodiment of the present invention includes one arm comprising a spring which is biased to assume an extended position. A sensor is fixed to the arm proximate a first end thereof. This catheter may also be used for mapping the locations of vulnerable plaque deposits within a blood vessel.

In a preferred embodiment, the sensor contacts the inner surface of the blood vessel when the arm is in the extended position. In this preferred embodiment, the temperature measured by the sensor may rise when the sensor is proximate to a vulnerable plaque deposit. Variations in the temperature measured by the sensor may be noted as the catheter is moved proximally and/or distally through the blood vessel, and these variations may be correlated to the axial position of vulnerable plaque deposits.

Variations in the signal from the sensor may also be noted as the catheter is rotated about it's longitudinal axis. These variations may be correlated to the angular location of vulnerable plaque deposits within the blood vessel.

Yet another exemplary embodiment of a catheter in accordance with the present invention includes a body member disposed about an elongate shaft of the catheter. The body member defines a plurality of flow channels and a temperature sensor is disposed within each channel. This catheter may also be used along with methods in accordance with the present invention for mapping the locations of vulnerable plaque deposits within the blood vessel.

The body member of the catheter is preferably sized so that an outer surface of the body member is disposed proximate the inner surface of the blood vessel. When this is the case, blood flowing proximate the inner surface of the blood vessel will flow into the channels. Sensors may be used to measure the temperature of the blood flowing through the channels. Blood which flows over a vulnerable plaque deposit will be warmed by the vulnerable plaque deposit. The increased temperature of this blood may be observed and/or recorded using the sensors disposed within the channels.

As the catheter is moved proximally and/or distally through the blood vessel, the distal end of the body member will be proximate different portions of the inner surface of the blood vessel. Variations in the signals from the sensors may be noted as the catheter is moved proximally and/or distally through the blood vessel, and these variations may be correlated to the axial position of the catheter. This information may be used to identify an axial component of the position of any vulnerable plaque deposits in the blood vessel.

The flow channels and the sensors are preferably disposed radially about the elongate shaft. An angular component of the position of plaque deposits within the blood vessel may be identified by observing variations between the signals from the different sensors. For example, sensors which are proximate vulnerable plaque deposits may read higher temperatures than sensors which are not proximate vulnerable plaque deposits.

BRIEF DESCRIPTION OF THE DRAWINGS

FIG. 4 is a perspective view of a catheter in accordance with yet another exemplary embodiment of the present invention;

FIG. 5 is a perspective view of a catheter in accordance with an exemplary embodiment of the present invention;

DETAILED DESCRIPTION OF THE INVENTION

The following detailed description should be read with reference to the drawings, in which like elements in different drawings are numbered in like fashion. The drawings which are not necessarily to scale, depict selected embodiments and are not intended to limit the scope of the invention. In some cases, the drawings may be highly diagrammatic in nature. Examples of constructions, materials, dimensions, and manufacturing processes are provided for various elements. Those skilled in the art will recognize that many of the examples provided have suitable alternatives which may be utilized.

Figure 1:
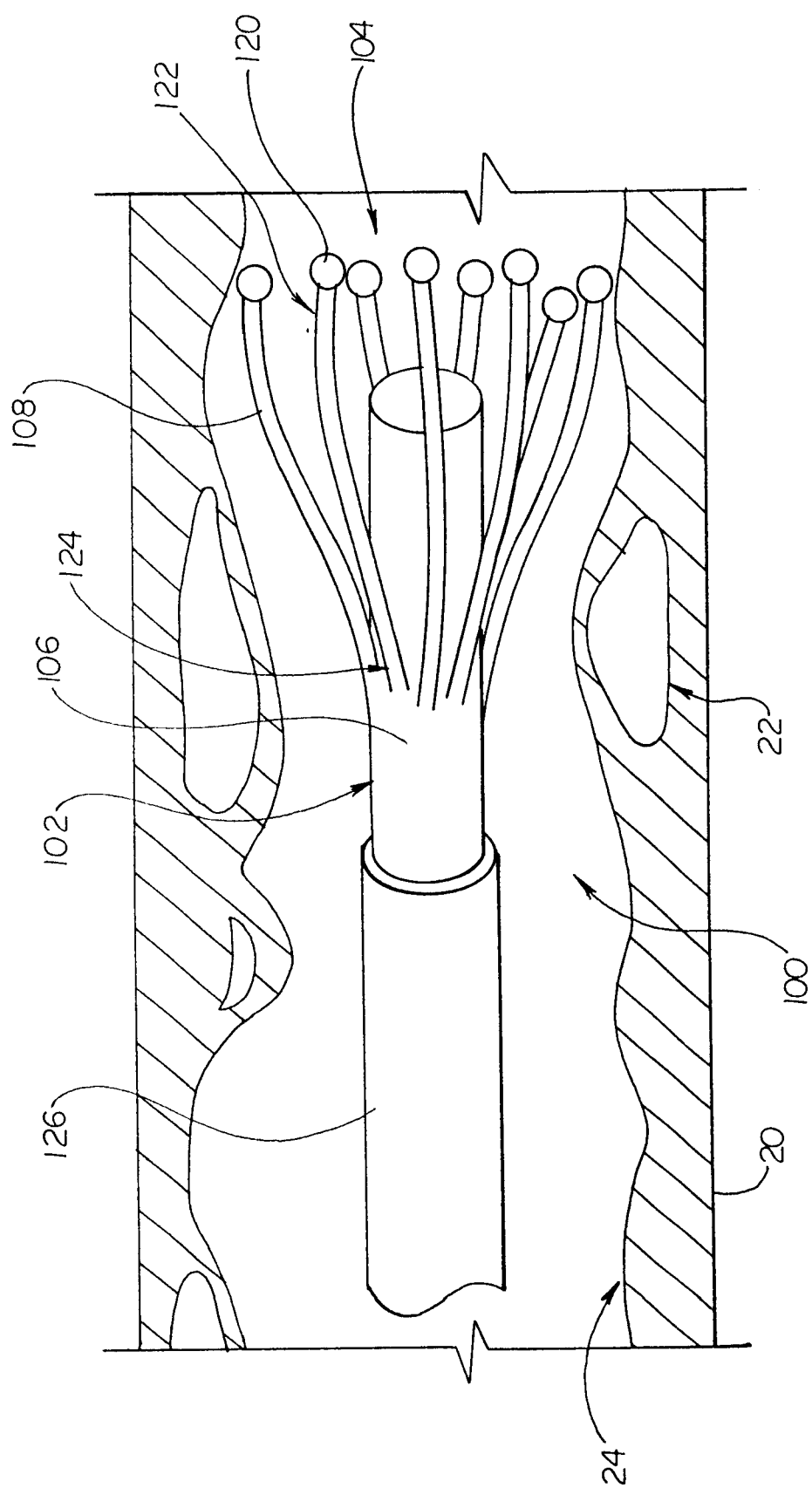
FIG. 1 is a perspective view of a catheter in accordance with an exemplary embodiment of the present invention.

FIG. 1 is a perspective view of a catheter 100 in accordance with an exemplary embodiment of the present invention. Catheter 100 may be used for mapping the locations of vulnerable plaque deposits 22 within a blood vessel 20. Catheter 100 comprises an elongate shaft 102 having a distal end 104, a proximal end (not shown in FIG. 1) and an outer surface 106. Catheter 100 also includes a plurality of arms 108. In the embodiment of FIG. 1, a sensor 120 is fixed to each arm 108 proximate a first end 122 thereof. A second end 124 of each arm 108 is fixed to elongate shaft 102.

Arms 108 preferably have an extended position and a retracted position. In the embodiment of FIG. 1, arms 108 are shown in the extended position. A sheath 126 is disposed about elongate shaft 102. Arms 108 may be urged into the retracted position by advancing sheath 126 distally along elongate shaft 102. In a preferred embodiment, each sensor 120 contacts inner surface 24 of blood vessel 20 when arms 108 are in the extended position.

Each sensor 120 may comprise a temperature sensor, an ultrasonic sensor, and/or an electromagnetic radiation sensor. In a preferred embodiment, each sensor 120 comprises a temperature sensor. Examples of temperature sensors which may be suitable in some applications include resistance temperature devices (RTS's), thermistors, thermocouples, MEMS (microelectrical mechanical systems), and microbolometers.

Blood vessel 20 includes a plurality of vulnerable plaque deposits 22. Each vulnerable plaque deposit includes a core portion 26 comprising a relatively soft material and a cap 28 overlaying the core. As catheter 100 is moved proximally and/or distally through blood vessel 20, sensors 120 preferably contact different portions of inner surface 24 of blood vessel 20.

The signal from each sensor 120 may be displayed and/or recorded using a suitable instrument. Variations in these signals may be noted as catheter 100 is moved proximally and/or distally through blood vessel 20. The variations in the sensor signal may be correlated with the axial position of catheter 100. This information may be used to identify the position of any vulnerable plaque deposits in blood vessel 20.

Figure 2:
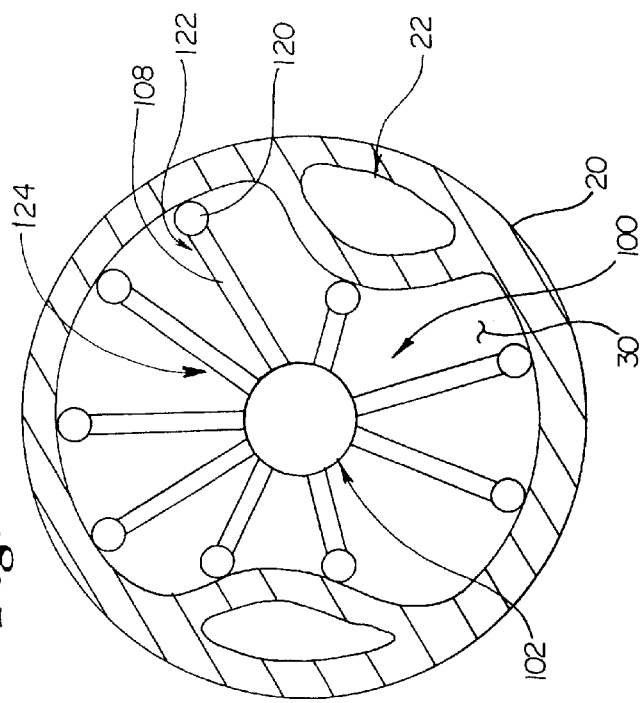
FIG. 2 is a lateral cross-sectional view of a blood vessel, and the catheter of FIG. 1 is shown disposed within a lumen defined by the blood vessel.

FIG. 2 is a lateral cross-sectional view of a blood vessel 20. Catheter 100 of FIG. 1 is shown disposed within a lumen 30 of blood vessel 20. Catheter 100 may be used for mapping the location of vulnerable plaque deposits 22 within a blood vessel 20 as described above. In FIG. 2, it may be appreciated that arms 108 of catheter 100 expand radially away from elongate shaft 102. A sensor 120 is fixed to each arm 108 proximate a first end 122 thereof. A second end 124 of each arm 108 is fixed to elongate shaft 102. The angular orientation of plaque deposits 22 within blood vessel 20 may be identified by observing variations between the signals from the different sensors 120. For example, sensors 120 which are proximate vulnerable plaque deposits 22 may read higher temperatures than sensors 120 which are not proximate vulnerable plaque deposits.

Figure 3:
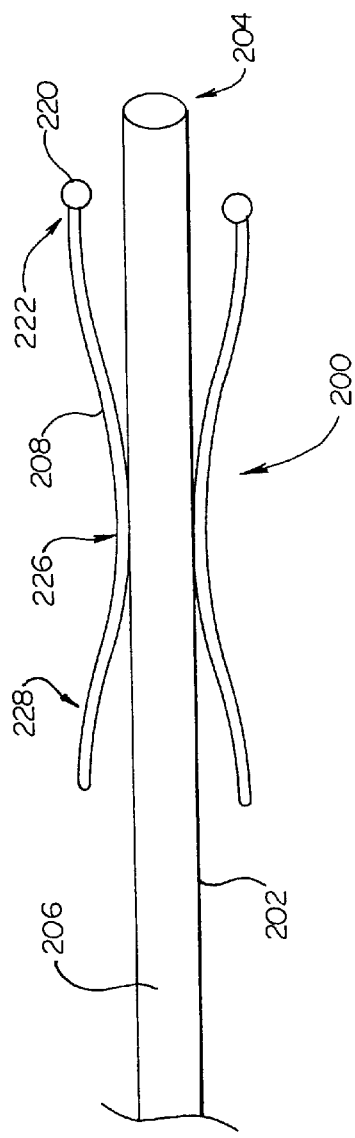
FIG. 3 is a plan view of a catheter in accordance with an additional exemplary embodiment of the present invention.

FIG. 3 is a plan view of a catheter 200 in accordance with an additional exemplary embodiment of the present invention. Catheter 200 comprises an elongate shaft 202 having a distal end 204, a proximal end (not shown in FIG. 3) and an outer surface 206. Catheter 200 also includes a plurality of arms 208. In the embodiment of FIG. 3, a sensor 220 is fixed to each arm 208 proximate a first end 222 thereof. A middle portion 226 of each arm 208 is fixed to elongate shaft 202 of catheter 200, and a free portion 228 of each arm 208 extends away from elongate shaft 202. In a preferred embodiment, free portions 228 of arms 208 act to stabilize the flow of blood when catheter 200 is disposed within a blood vessel. In the embodiment of FIG. 3, arms 208 are shown in the extended position. Arms 208 preferably have an extended position and a retracted position.

FIG. 4 is a perspective view of a catheter 300 in accordance with yet another exemplary embodiment of the present invention. Catheter 300 may be used for mapping the locations of vulnerable plaque deposits within a blood vessel. Catheter 300 comprises an elongate shaft 302 having a distal end 304, a proximal end (not shown in FIG. 4) and an outer surface 306.

A sheath 326 is slidingly disposed about a portion of elongate shaft 302. The first ends 322 of a plurality of arms 308 are fixed to sheath 326. The second end 324 of each arm 308 is fixed to a body member 330 of catheter 300. In the embodiment of FIG. 4, body member 330 is disposed about elongate shaft 302 proximate distal end 304. A sensor 320 is fixed to each arm 308 between first end 322 and second end 324. In the embodiment of FIG. 4, arms 308 are shown in the extended position. In a preferred embodiment, arms 308 are biased to assume the extended position. Arms 308 may be urged into a retracted position by moving sheath 326 proximally relative to elongate shaft 302. Arms 308 may also be urged into the extended position by moving sheath 326 distally relative to elongate shaft 302. In a preferred embodiment, each sensor 320 contacts the inner surface of a blood vessel when arms 308 are in the extended position.

Each sensor 320 may comprise various sensor types without deviating from the spirit and scope of the present invention. Examples of sensors which may be suitable in some applications include pressure sensors, ultrasonic sensors, electromagnetic radiation sensors, and temperature sensors. In a preferred embodiment, each sensor 320 comprises a temperature sensor. Temperature sensors which may be suitable in some applications, include resistance temperature devices (RTD's), thermistors, thermocouples, and MEMS.

FIG. 5 is a perspective view of a catheter 400 in accordance with an exemplary embodiment of the present invention. Catheter 400 also includes an arm 408 comprising spring 432 which is biased to assume the extended position shown in FIG. 5. A sensor 420 is fixed to arm 408 proximate a first end 422 thereof. A second end 424 of arm 408 is fixed to an elongate shaft 402. Elongate shaft 402 includes a distal end 404, a proximal end (not shown in FIG. 5) and an outer surface 406.

In FIG. 5, catheter 400 is shown disposed within a blood vessel 20 having vulnerable plaque deposits 22. Catheter 400 may be used for mapping the locations of the vulnerable plaque deposits 22 within blood vessel 20. In a preferred embodiment, sensor 420 contacts inner surface 24 of blood vessel 20 when arm 408 is in the extended position shown in FIG. 5. In this preferred embodiment, the temperature measured by sensor 420 may rise when sensor 420 is proximate a vulnerable plaque deposit 22.

Each vulnerable plaque deposit shown in FIG. 5 includes a core portion 26 comprising a relatively soft material and a cap 28 overlaying the core. As catheter 400 is moved proximally and/or distally through blood vessel 20, sensors 420 preferably contact different portions of inner surface 24 of blood vessel 20.

The signal from sensor 420 may be displayed and/or recorded using a suitable instrument. Variations in the signal may be noted as catheter 400 is moved proximally and/or distally through blood vessel 20, and these variations may be correlated with the axial position of catheter 400. Variations in the signal from sensor 420 may also be noted as catheter 400 is rotated about it's longitudinal axis. These variations may be correlated with the angular orientation of catheter 400. The information collected from sensor 420 may be used to identify the position of any vulnerable plaque deposits in blood vessel 20.

Figure 6:
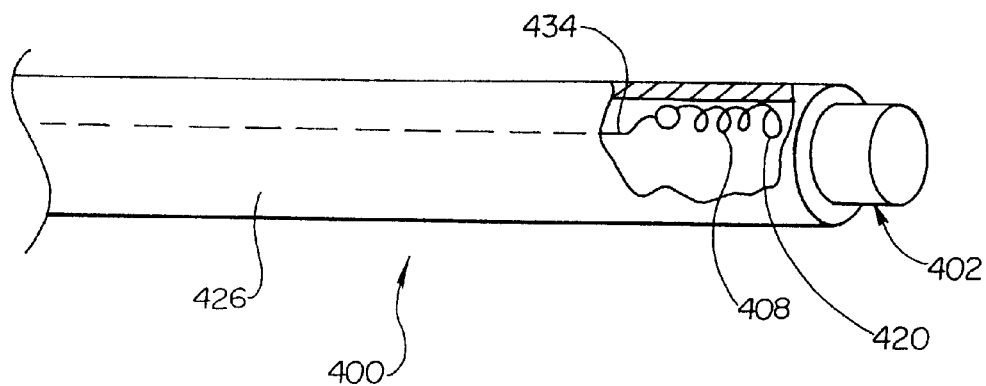
FIG. 6 is a partial cross sectional view of the catheter of FIG. 5.

FIG. 6 is a partial cross sectional view of catheter 400 of FIG. 5. In FIG. 6, it may be appreciated that catheter 400 includes a sheath 426 which is disposed about elongate shaft 402. In the embodiment of FIG. 6, sheath 426 has been advanced distally along elongate shaft 402 so that arm 408 of catheter 400 is disposed in a retracted position. In FIG. 6 it may be appreciated that catheter 400 includes a cable 434 disposed between sheath 426 and elongate shaft 402. A distal end of cable 434 is preferably coupled to sensor 420 and a proximal end of cable 434 is preferably coupled to an instrument which is adapted to display and/or record a signal from sensor 420. It is to be appreciated, that cable 434 may include any number of conductors. In some applications, the number of conductors may be selected to match sensor 420. For example, sensor 420 may comprise a thermocouple having two contacts which are coupled to two conductors of cable 434.

Figure 7:
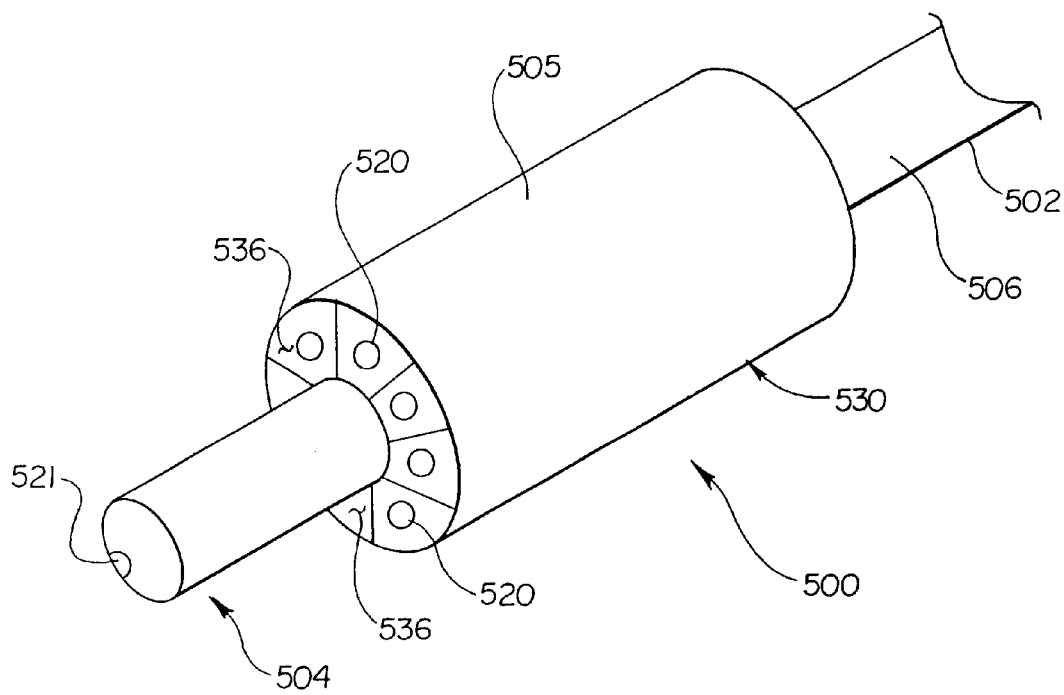
FIG. 7 is a perspective view of a catheter in accordance with still another exemplary embodiment of the present invention.

FIG. 7 is a perspective view of a catheter 500 in accordance with still another exemplary embodiment of the present invention. Catheter 500 comprises an elongate shaft 502 having a distal end 504, a proximal end (not shown in FIG. 7) and an outer surface 506. A body member 530 of catheter 500 is disposed about elongate shaft 502. Body member 530 defines a plurality of flow channels 536.

In the embodiment of FIG. 7, a sensor 520 is disposed within each flow channel 536. Catheter 500 also includes a reference sensor 521 disposed proximate distal end 504 of elongate shaft 502. Sensors 520 and 521 preferably comprise temperature sensors. Examples of temperature sensors which may be suitable in some applications include resistance temperature devices (RTD's), thermistors, and thermocouples.

Catheter 500 may be used for mapping the locations of vulnerable plaque deposits within a blood vessel. Body member 530 is preferably sized so that an outer surface 505 of body member 530 is disposed proximate the inner surface of a blood vessel. When this is the case, blood flowing proximate the inner surface of the blood vessel will flow into the channels. Sensors 520 may be used to measure the temperature of the blood flowing through the channels. Blood which flows over a vulnerable plaque deposit will be warmed by the vulnerable plaque deposit. The increased temperature of this blood may be observed and/or recorded using sensors 520.

As catheter 500 is moved proximally and/or distally through a blood vessel, the distal end of body member 530 will be proximate different portions of the inner surface of the blood vessel. Variations in the signals from the sensors may be noted as catheter 500 is moved proximally and/or distally through the blood vessel, and these variations may be correlated with the axial position of catheter 500. This information may be used to identify an axial component of the position of any vulnerable plaque deposits in the blood vessel.

In FIG. 7, it may be appreciated that flow channels 536 and sensors 520 are disposed radially about elongate shaft 502. An angular component of the position of plaque deposits within the blood vessel may be identified by observing variations between the signals from the different sensors 520. For example, sensors 520 which are proximate vulnerable plaque deposits may read higher temperatures than sensors 520 which are not proximate vulnerable plaque deposits.

Figure 8:
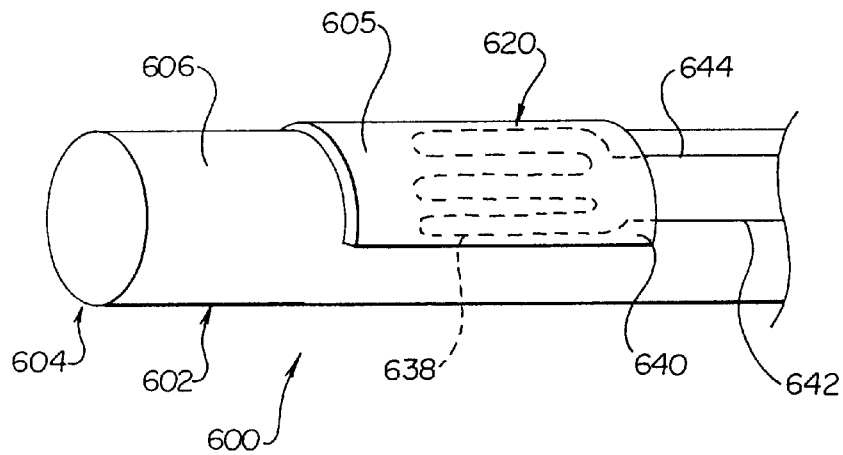
FIG. 8 is a perspective view of a catheter in accordance with still another exemplary embodiment of the present invention.

FIG. 8 is a perspective view of a catheter 600 in accordance with still another exemplary embodiment of the present invention. Catheter 600 may be used for mapping the locations of vulnerable plaque deposits within a blood vessel. Catheter 600 comprises an elongate shaft 602 having a distal end 604, a proximal end (not shown in FIG. 8) and an outer surface 606. A sensor 620 is disposed so that it overlays outer surface 606 of elongate shaft 602. In the embodiment of FIG. 8, sensor 620 comprises a flexible substrate 640 and a conductive path 638. Conductive path 638 is coupled to a first conductor 642 and a second conductor 644. In a preferred embodiment, the electrical resistance of conductive path 638 varies with temperature. Also in a preferred embodiment, first conductor 642 and a second conductor 644 are insulated. First conductor 642 and second conductor 644 may be insulated, for example, by a layer of shrink tubing overlaying elongate shaft 602. In the embodiment of FIG. 8, sensor 620 has a generally cylindrical outer surface 605. In a preferred embodiment, the shape of outer surface 605 is selected so that sensor 620 contacts the inner surface of a blood vessel across a substantial area.

Figure 9:
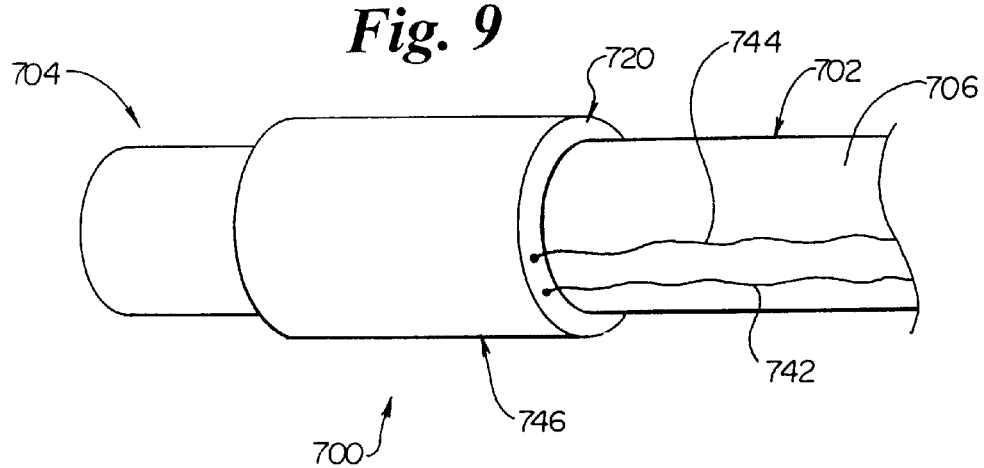
FIG. 9 is a perspective view of a catheter in accordance with still another exemplary embodiment of the present invention.

FIG. 9 is a perspective view of a catheter 700 in accordance with still another exemplary embodiment of the present invention. Catheter 700 may be used for mapping the locations of vulnerable plaque deposits within a blood vessel. Catheter 700 comprises an elongate shaft 702 having a distal end 704, a proximal end (not shown in FIG. 9) and an outer surface 706. Catheter 700 also includes a sensor 720 disposed proximate distal end 704 of elongate shaft 702. In the embodiment of FIG. 9, sensor 720 comprises a body 746 having a generally cylindrical shape. In a preferred embodiment, the shape of body 746 is selected so that sensor 720 contacts the inner surface of a blood vessel across a substantial area. A first conductor 742 and a second conductor 744 are coupled to sensor 720. In a preferred embodiment, a temperature recording and displaying instrument may interrogate sensor 720 via first conductor 742 and second conductor 744.

Figure 10:
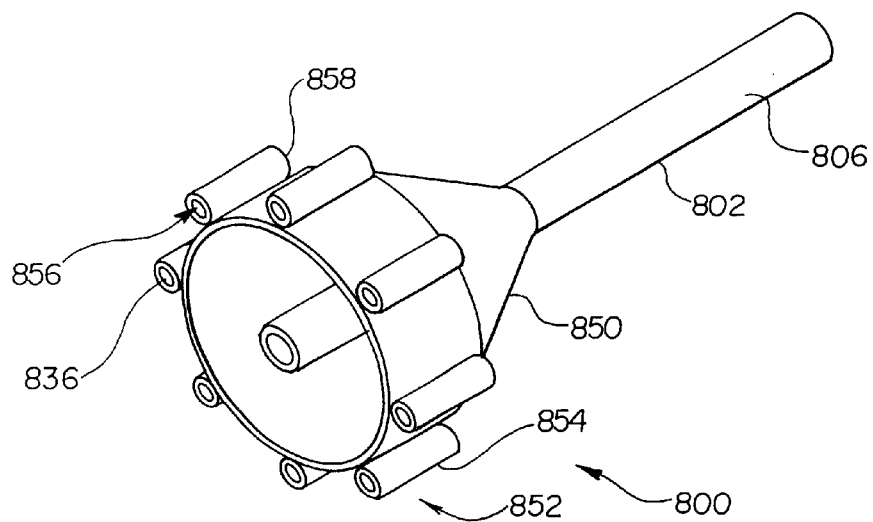
FIG. 10 is a cross sectional perspective view of a catheter in accordance with still another exemplary embodiment of the present invention.

FIG. 10 is a cross sectional perspective view of a catheter 800 in accordance with still another exemplary embodiment of the present invention. Catheter 800 comprises an elongate shaft 802 having an outer surface 806. An interstitial member such as balloon 850 of catheter 800 is disposed about elongate shaft 802.

Catheter 800 also includes an array 852 comprising plurality of cowls 854 circumferentially disposed about balloon 850. Cowls 854 are preferably fixed to balloon 850. Each cowl 854 defines an inlet port 856, an outlet port 858, and a flow channel 836 extending therebetween.

A sensor 820 (not shown in FIG. 10) is preferably disposed within each flow channel 836. Each sensor 820 preferably comprises a temperature sensor. Examples of temperature sensors which may be suitable in some applications include resistance temperature devices (RTD's), thermistors, and thermocouples.

Balloon 850 preferably has an inflated state and a deflated state. In the embodiment of FIG. 10, balloon 850 is disposed outside of a blood vessel, and is shown in an inflated state. In a preferred embodiment, balloon 850 is configured such that cowls 854 are urged radically away from elongate shaft 802 when balloon 850 is in the inflated state. Alternatively, the cowls may be radically extended by a different mechanical mechanism, such as by a plurality of resilient arms, each arm being attached at one end to a cowl 854 and at an opposite end to the elongate shaft 802.

Figure 11:
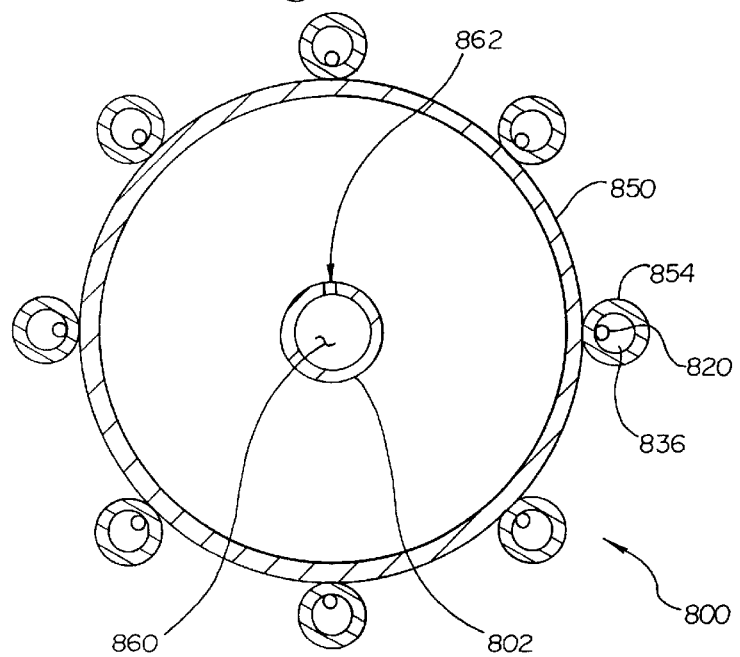
FIG. 11 is a cross sectional plan view of the catheter of FIG. 10.

FIG. 11 is a cross sectional plan view of catheter 800 of FIG. 10. In FIG. 11, a sensor 820 may be seen disposed within each flow channel 836. Each flow channel 836 is defined by a cowl 854 that is preferably fixed to balloon 850. Balloon 850 is disposed about elongate shaft 802.

In the embodiment of FIG. 11, balloon 850 is disposed outside of a blood vessel, and is shown in an inflated state. Balloon 850 may be inflated, for example, by urging a fluid through an inflation lumen 860 and an inflation port 862 defined by elongate shaft 802.

Balloon 850 is preferably configured such that cowls 854 will be urged against the inner surface of a blood vessel when balloon 850 is placed in the inflated state while catheter 800 is disposed within the blood vessel. Balloon 850 is preferably configured such that blood flow around cowls 854 will be precluded when balloon 850 is in the inflated state.

Blood flowing proximate the inner surface of the blood vessel preferably flows through flow channels 836 defined by cowls 854. Sensors 820 may be used to measure the temperature of the blood flowing through the channels. Blood which flows over a vulnerable plaque deposit will be warmed by the vulnerable plaque deposit. The increased temperature of this blood may be observed and/or recorded using sensors 820.

Figure 12:
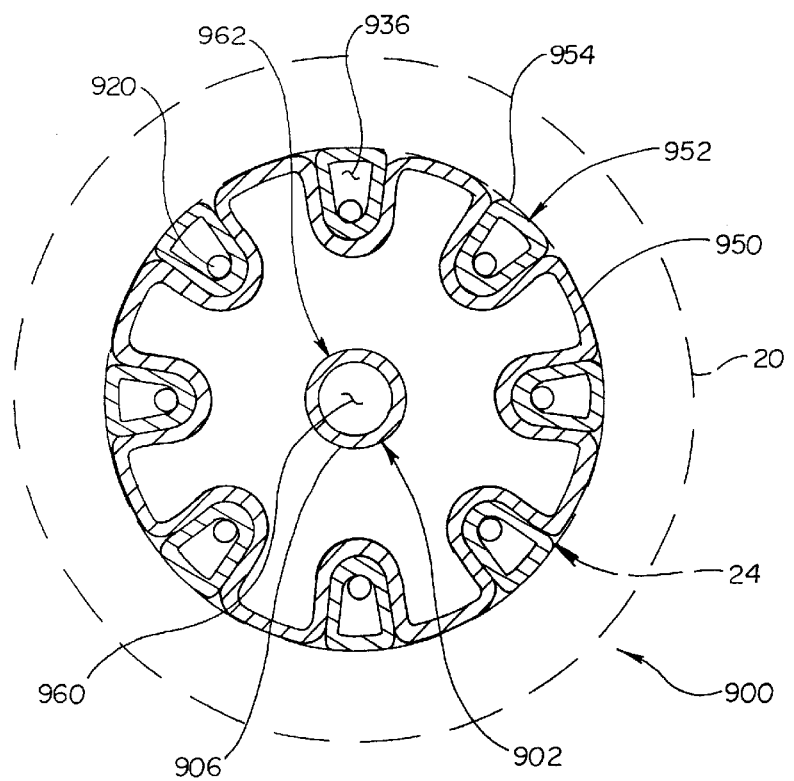
FIG. 12 is a cross sectional plan view of a catheter in accordance with yet another exemplary embodiment of the present invention.

FIG. 12 is a cross sectional plan view of a catheter 900 in accordance with yet another exemplary embodiment of the present invention. Catheter 900 comprises an elongate shaft 902 having an outer surface 906. A balloon 950 of catheter 900 is disposed about elongate shaft 902.

Catheter 900 also includes a array 952 comprising plurality of cowls 954 circumferentially disposed about balloon 950. In the embodiment of FIG. 12, each cowl has a generally wedge shaped cross-sectional shape. Each cowl 954 is preferably fixed to balloon 950.

Each cowl 954 defines a flow channel 936. A sensor 920 is preferably disposed within each flow channel 936. Each sensor 920 preferably comprises a temperature sensor. Examples of temperature sensors which may be suitable in some applications include resistance temperature devices (RTD's), thermistors, and thermocouples.

Balloon 950 preferably has an inflated state and a deflated state. In the embodiment of FIG. 12, balloon 950 is disposed within a blood vessel 20, and is shown in an inflated state. In a preferred embodiment, balloon 950 is configured such that cowls 954 are urged radially away from elongate shaft 902 when balloon 950 is in the inflated state. In FIG. 12, it may be appreciated that cowls 954 have been urged against an inner surface 24 of blood vessel 20 by balloon 950. Balloon 950 may be inflated, for example, by urging a fluid through an inflation lumen 960 and an inflation port 962 defined by elongate shaft 902.

Balloon 950 is preferably configured such that blood flow around cowls 954 will be precluded when balloon 950 is in the inflated state. Blood flowing proximate inner surface 24 of blood vessel 20 preferably flows into flow channels 936 defined by cowls 954. Sensors 920 may be used to measure the temperature of the blood flowing through the channels. Blood which flows over a vulnerable plaque deposit will be warmed by the vulnerable plaque deposit. The increased temperature of this blood may be observed and/or recorded using sensors 920.

Having thus described the preferred embodiments of the present invention, those of skill in the art will readily appreciate that yet other embodiments may be made and used within the scope of the claims hereto attached. Numerous advantages of the invention covered by this document have been set forth in the foregoing description. It will be understood, however, that this disclosure is, in many respects, only illustrative. Changes may be made in details, particularly in matters of shape, size, and arrangement of parts without exceeding the scope of the invention. The invention's scope is, of course, defined in the language in which the appended claims are expressed.

What is claimed is:

1. A catheter for mapping vulnerable plaque deposits within a blood vessel, comprising;
    an elongate shaft having a proximal end and a distal end;
    at least one cowl fixed to the elongate shaft proximate the distal end thereof;
    the at least one cowl defining an inlet port, an outlet port, and a fluid flow channel extending therebetween; and
    at least one temperature sensor disposed within the flow channel defined by the at least one cowl.

2. The catheter of claim 1, wherein the at least one temperature sensor is adapted to measure the temperature of blood passing through the flow channel.

3. The catheter of claim 1, wherein the at least one temperature sensor is adapted to measure the temperature of blood passing through the flow channel; and
    the at least one cowl is configured such that the temperature of the blood passing through the flow channel is reflective of the temperature of an inner surface of the blood vessel proximate the distal end; of the catheter.

4. The catheter of claim 1, wherein the temperature sensor comprises a resistance temperature device.

5. The catheter of claim 1, wherein the temperature sensor comprises a thermocouple.

6. The catheter of claim 1, wherein the temperature sensor comprises a thermistor.

7. The catheter of claim 1, wherein the temperature sensor comprises a microbolometer.

8. The catheter of claim 1, further comprising an interstitial member disposed between the at least one cowl and the elongate shaft.

9. The catheter of claim 1, further comprising a balloon disposed between the at least one cowl and the elongate shaft.

10. The catheter of claim 9, wherein the balloon has an inflated state and a deflated state.

11. The catheter of claim 10, wherein the balloon is configured such that flow of blood around the at least one cowl is precluded when the balloon is in the inflated state.

12. The catheter of claim 10, wherein the balloon is configured such that the at least one cowl is urged radially away from the elongate shaft when the balloon is in the inflated state.

13. The catheter of claim 1, further comprising a plurality of cowls radially disposed about the elongate shaft.

14. A catheter for mapping vulnerable plaque deposits within a blood vessel, comprising;
    an elongate shaft having a proximal end and a distal end;
    a plurality of cowls radially disposed about the elongate shaft proximate the distal end thereof;
    each cowl defining an inlet port, an outlet port, and a fluid flow channel extending therebetween; and
    a temperature sensor disposed within each flow channel.

15. The catheter of claim 14, wherein each temperature sensor comprises a resistance temperature device.

16. The catheter of claim 14, wherein each temperature sensor comprises a thermocouple.

17. The catheter of claim 14, wherein each temperature sensor comprises a thermistor.

18. The catheter of claim 14, wherein each temperature sensor comprises a microbolometer.

19. The catheter of claim 14, further comprising an interstitial member disposed between the cowls and the elongate shaft.

20. The catheter of claim 14, further comprising a balloon disposed between the plurality of cowls and the elongate shaft.

21. The catheter of claim 20, wherein the balloon has an inflated state and a deflated state.

22. The catheter of claim 21, wherein the balloon is configured such that flow of blood around the cowls is precluded when the balloon is in the inflated state.

23. The catheter of claim 21, wherein the balloon is configured such that the cowls are urged radially away from the elongate shaft when the balloon is in the inflated state.

24. A catheter for mapping vulnerable plaque deposits within a blood vessel, comprising;
    an elongate shaft having a proximal end and a distal end;
    an array of cowls radially disposed about the elongate shaft proximate the distal end thereof;
    each cowl of the array of cowls defining an inlet port, an outlet port, and a fluid flow channel extending therebetween;
    a temperature sensor disposed within each flow channel; and
    a means for radially expanding the array of cowls.

25. The catheter of claim 24, wherein each temperature sensor comprises a resistance temperature device.

26. The catheter of claim 24, wherein each temperature sensor comprises a thermocouple.

27. The catheter of claim 24, wherein each temperature sensor comprises a thermistor.

28. The catheter of claim 24, wherein each temperature sensor comprises a microbolometer.

29. The catheter of claim 24, wherein the means for radially expanding the array of cowls comprises a hydraulic mechanism.

30. The catheter of claim 29, wherein the hydraulic mechanism comprises a balloon.

31. The catheter of claim 30, wherein the balloon is configured such that flow of blood around the cowls is precluded when the balloon is in an inflated state.

32. The catheter of claim 24, wherein the means for radially expanding the array of cowls comprises a mechanical mechanism.

33. The catheter of claim 24, wherein the means for radially expanding the array of cowls comprises a plurality of resilient arms.

* * * * *